(12) United States Patent
Francescatti et al.

(10) Patent No.: US 8,529,427 B2
(45) Date of Patent: *Sep. 10, 2013

(54) APPLICATORS AND METHODS FOR INTRAOPERATIVE TREATMENT OF PROLIFERATIVE DISEASES OF THE BREAST

(71) Applicant: Xoft, Inc., Sunnyvale, CA (US)

(72) Inventors: Darius Francescatti, Barrington, IL (US); James E. Jervis, Atherton, CA (US)

(73) Assignee: Xoft, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/649,257

(22) Filed: Oct. 11, 2012

(65) Prior Publication Data

US 2013/0035536 A1 Feb. 7, 2013

Related U.S. Application Data

(63) Continuation of application No. 12/156,298, filed on May 30, 2008, now Pat. No. 8,303,476.

(51) Int. Cl.
*A61N 5/01* (2006.01)
(52) U.S. Cl.
USPC .................................................. 600/3; 600/1
(58) Field of Classification Search
USPC ........................................................ 600/1, 3
See application file for complete search history.

(56) References Cited

U.S. PATENT DOCUMENTS

| 4,197,860 | A | * | 4/1980 | Sterzer | 607/156 |
| 4,584,991 | A | * | 4/1986 | Tokita et al. | 600/3 |
| 6,601,740 | B1 | * | 8/2003 | Clive | 222/484 |
| 6,810,109 | B2 | * | 10/2004 | Chornenky | 378/108 |
| 2002/0087206 | A1 | | 7/2002 | Hirschberg et al. | |
| 2003/0225331 | A1 | * | 12/2003 | Diederich et al. | 600/437 |
| 2007/0167666 | A1 | | 7/2007 | Lubock et al. | |
| 2007/0191667 | A1 | | 8/2007 | Lubock et al. | |
| 2007/0219446 | A1 | | 9/2007 | Beyhan | |

FOREIGN PATENT DOCUMENTS

EP 1616597 A1 1/2006

* cited by examiner

*Primary Examiner* — Christine Matthews
*Assistant Examiner* — Joshua D Lannu
(74) *Attorney, Agent, or Firm* — Loginov & Associates, PLLC; William A. Loginov

(57) ABSTRACT

A device for administering brachytherapy to a patient includes a vessel that may be in the form of a hollow cylindrical cup, for fleshing into and substantially filling the open-ended cavity. The vessel has a closed outer end, which may be a removable cover, and a source guide penetrates the closed outer end so as to extend deep into the vessel, to receive a radiation source in the source guide. A manipulator can be connected to the radiation source, and also to the source guide, for allowing several different types of manipulation of the source orientation and position within the vessel during the brachytherapy procedure.

15 Claims, 6 Drawing Sheets

APPLICATORS AND METHODS FOR INTRAOPERATIVE TREATMENT OF PROLIFERATIVE DISEASES OF THE BREAST

RELATED APPLICATIONS

This application is a continuation of co-pending U.S. patent application Ser. No. 12/156,298, filed May 30, 2008, entitled APPLICATORS AND METHODS FOR INTRAOPERATIVE TREATMENT OF PROLIFERATIVE DISEASES OF THE BREAST, the entire disclosure of which is herein incorporated by reference.

BACKGROUND OF THE INVENTION

This invention relates to radiation therapy of proliferative disease as required adjuvant care following surgical resection of tumors or other pathological conditions. More particularly, it pertains to the intraoperative application of therapeutic radiation emitted from radiation sources positioned within the resection cavity created by surgical resection. Discussion herein is largely directed to radiotherapy following at least partial resection of breast tumors, but it is to be understood that the apparatus and methods may be applied to different anatomical sites.

It has been demonstrated in many areas of surgical oncology that adjuvant radiation treatment following tumor resection reduces the likelihood of recurrence of cancer or other proliferative disease. The likelihood of infiltrative disease decreases with distance from a primary site in a tissue with confirmed disease. It has also been shown that brachytherapy delivered from within the resection cavity is as effective as external beam therapy, reduces exposure of normal tissue to inadvertent radiation exposure, and furthermore, that quality of life is superior after brachytherapy compared to that following external beam therapy. It is therefore desirable that brachytherapy or brachytherapy-like techniques be made available to as great a population of patients as possible.

Many radiotherapists prefer to deliver radiotherapy in fractions spaced in time (over a period of several days or even weeks) using intracavitary brachytherapy techniques to take advantage of the fact that normal cells recover from radiation exposure in a shorter period of time than diseased cells. Other radiotherapists have found intraoperative radiation therapy (IORT, radiotherapy delivered during the same operative procedure as the tumor resection) to be equally if not more effective in many circumstances, and may offer the opportunity for simultaneous reconstructive surgery. This invention pertains to IORT, or delivery of other single-treatment radiotherapy wherein a complete treatment or prescription is delivered from the resection cavity in one dose during a conventional open surgical procedure. It has also been demonstrated that radiation intensity diminishes with distance from the radiation source. Radiotherapists fairly universally have therefore found that it is generally desirable to spatially separate the radiation source from the tissues being treated. This reduces the likelihood of exposing normal tissue to harmful levels of radiation, particularly that tissue nearest the radiation source, while still delivering the prescribed radiation to the prescribed depth. In a situation where the resection cavity is substantially centered on the site of the tumor, the prescription depth is the depth in tissue outside the resection cavity where the likelihood of undiagnosed disease is highest and where adjuvant radiation treatment is warranted. The target tissue is the tissue to which this prophylactic radiotherapy is directed, generally lying outside the resection cavity, but within the bounds of the prescription depth. Where the cavity (and hence the resected tissue specimen) is eccentric about the tumor location, that portion of the cavity farthest from the tumor may require less radiation prescription depth than tissues near the resected tumor location.

To create this spatial separation in traditional intracavitary brachytherapy, an applicator, usually comprising a balloon, is positioned and inflated within the resection cavity. For the same reasons as above, it is also desirable to create spatial separation preparatory to IORT treatment within an open surgical cavity. At present, however, there are no applicators, analogous to the balloon applicators described above, for use with IORT methods in open surgical fields. A purpose of this invention is to fill that need.

Traditional brachytherapy sources are isotopic seeds, often of iridium 192 positioned on wires, which are manipulated within applicator source guides and balloons to deliver the prescribed treatment to the target tissue surrounding the balloon and resection cavity. Emissions from iridium and other common medical isotopes usually have high-energy components which can penetrate deeply into tissue. They also emit continuously, and thus can only be used in special, heavily-shielded rooms. In addition, concerns for the safety of personnel require isolation of the patient during treatment, shielded storage at all other times, and automated handling between the storage chamber and the applicator when in the patient. In total, the capital expense required for such facilities dictates that treatment centers be located in urban areas so as to serve sizeable patient populations. This can result in under serving rural patients who cannot repeatedly travel to urban treatment centers for a course of prolonged radiation treatment. Furthermore, the need for patient isolation is inconvenient for therapists, not to mention daunting for the patients under treatment. With such brachytherapy, it is clear that any improvements to the total duration of treatment, cost, source handling and shielding difficulties, patient fear factors and inconvenience would be welcome.

Recently, miniature electronic x-ray tubes have provided a preferable alternative to use of isotopes. Such tubes do not emit continuously, they only emit when powered in a manner causing emission and they can be turned on and off, or if desired, modulated such that their penetration depth can be controlled (by control of acceleration voltage) and their dose intensity can be controlled (by filament current) as well. One reference describing the principles and construction of such tubes is Atoms, Radiation and Radiation Protection, Second Edition, John E. Turner, Ph.D., CHP, 1995, John Wiley & Sons, Section 2.10. Electronic brachytherapy sources generally require cooling and are usually contained in a fixed position within a catheter designed for the purpose, but otherwise are more versatile and convenient to use than isotopes, and can be engineered to accommodate a wide variety of dosimetric prescription detail. In addition miniature x-ray tubes can be designed to emit substantially isotropically, or directed to emit only through a predetermined solid angle, permitting more detailed treatment plans. Isotope radiation cannot be controlled in this manner. Furthermore, the x-ray energy spectrum in ranges suitable for brachytherapy or IORT eliminates the need for heavily shielded structures, or "bunkers", and also permits the therapist to be in the room with the patient during therapy. Therapy can proceed in almost any medical facility, urban, rural or even mobile, and therefore, with miniature x-ray tubes, a greater population of patients can be treated, and the costs of therapy are greatly reduced. It is clear that electronic brachytherapy sources have already contributed significantly to making such therapy more readily available and cost effective than other methods.

Treatment duration can still be improved, however, and IORT is a procedure directed to this end.

Tumor resection is usually carried out by open surgical technique where the surgeon proceeds directly through skin and tissue overlying the tumor, or at the surgeon's discretion, from a nearby point which may provide more pleasing cosmeses. The incision must accommodate tumor resection including excision of additional tissue around the tumor, the margins of which are believed to be disease free. Often, efforts are made to provide markers which help orient the tissue with respect to the cavity from which it was excised, and which provide a basis the pathologist and surgeon can use to communicate with respect to the precise location of the tumor within the specimen (thus the cavity) and/or the location of further disease at the margins. Once analyzed, and if necessary, further tissue is removed until the margins are "clear", or free of apparent disease. In some modern institutions, this pathologic assessment is performed while the patient is still anaesthetized and on the operating table. Once the margins are determined to be free of disease, if IORT is the radiotherapy of choice, it is then administered.

Because the extent of the disease is uncertain at the outset of surgery, the incremental nature of the resection procedure in response to pathological findings may result in a cavity, the boundaries of which are eccentric with respect to tumor, and some margins which are relatively farther removed from the original tumor than others, and thus less likely to be infiltrated with disease. In such a circumstance, the prescription dose can be specified for delivery to an imaginary surface defined in relation the tumor location without reference to the cavity boundaries. It is an object of this invention to accommodate such eccentricity so that tissues lying farthest from the tumor receive a lower dose than those lying near the tumor site, and to facilitate preparation of such a treatment plan.

Other objectives of the invention will become apparent from the following summary, drawings and description.

SUMMARY OF THE INVENTION

This invention is intended particularly for the breast and comprises a rigid cup of predetermined shape, the sides of which are transparent to radiation and visible light, and the bottom of which is optionally attenuating in order to shield the underlying tissues and organs from harmful radiation. The cup is placed into the cavity, bottom first, and advanced until it reaches the bottom of the cavity. The cup is configured so as to substantially fill and shape the cavity. If desired, the cup can be sutured near its base to secure it to the bottom of the cavity. After being so placed, the conformance of the cavity tissue to the cup can be visually ascertained, and if necessary adjusted appropriately to eliminate voids or pockets of air or seroma. Alternatively, the surrounding tissue can be urged into conformance with the sides of the cup and held in place by conventional tapes and/or sutures, by selecting a differently shaped rigid cup, or by other methods including provision of a matrix on the outside of the cup for application of suction to draw breast tissue into conformance with the cup and so retain it during radiotherapy.

The invention further comprises a lid to cover the cup and a connection with a gasket or other conventional features proximate to the cup lip to create a fluid tight seal between the two elements. Near or at the periphery of the lid is a radiation attenuating skirt extending distally into the cup or just outside the cup (with securement threads for engaging the cup) to shield the skin and near-skin tissue gathered around the cup from radiation. If desired, the entire lid (or lid assembly if comprised of multiple elements) can be attenuating to protect those nearby during radiotherapy delivery. Extending through the lid is a tubular source guide which is radiation transparent and reaches sufficiently into the cup such that a radiation source can deliver as therapeutic dose. In one embodiment, the source can be manipulated within the guide (such positioning herein referred to as along the "Z" axis of the applicator or cavity) to effectively deliver the prescribed radiation. The distal end of the source guide is closed. Proximally, the guide extends outward of the lid to an open end where a source and catheter can be inserted. If source manipulation is desired, the proximal end of the source guide further comprises a flexible extension which can be secured to the source manipulator located outside the patient in order to provide a fixed reference distance between the outside manipulation apparatus to the patient and applicator. Such a flexible connection can accommodate patient motion, for example motion due to respiration, without introducing error in source positioning.

In simplest form, the cup is circular and the source guide is normal to the lid and located centrally to position the source equidistant from the sides of the cup in order for a substantially isotropic source to produce a laterally uniform isodose pattern. Other lid shapes and source guide positioning can be used to accommodate irregular cavity shapes and/or non-uniform prescription situations, and even source guide positions which are varied during the radiotherapy procedure. If the source position is to be varied laterally in the X and/or Y directions, the surface of the lid can comprise a membrane to which the source guide is secured and sealed, and which can accommodate the desired changes in position, X/Y or angular. Conventional servo-systems can provide such manipulation in response to computer commands, and with source positioning within the source guide along the Z axis, can position the source at any location within the cup.

Delivery of radiotherapy using such a system is preceded by a treatment planning procedure in which the anatomy and applicator apparatus may be imaged using conventional methods, usually either x-ray or CT, but since the cup is transparent and its shape is known, direct visualization may be adequate to check for tissue conformance to the cup such that the tissue can be gathered more effectively around the cup, and to identify the presence of pockets of air or seroma between the cup and tissue. Once the geometrical relationships are confirmed, the desired therapy can be planned and the source position(s) and/or manipulation determined. Ultimately, control parameters for the apparatus are programmed to produce the plan for use during treatment. Prior to treatment, and if desired before imaging and planning, the volume within the cup and lid is filled with an attenuating medium, preferably saline, and air from within the volume is vented if necessary. Next, a radiation shield or shields, perhaps with a hole to accommodate exit of the source guide, are draped on the patient around the applicator apparatus as necessary to protect those nearby during treatment. (See U.S. patent application Ser. No. 11/323,331.) The source is then inserted into the applicator, connected to the positioning control apparatus, if any, and treatment initiated. After delivery of the prescription, the source and other apparatus are removed. If any intraoperative reconstruction is indicated, it is performed, and the cavity is then closed surgically in a conventional manner.

If desired, radiation sensors can be mounted on the skin or on the applicator apparatus to assist in dose determination during the treatment planning process, or to monitor treatment to plan and/or warn of overdose during radiotherapy.

Although the description herein assumes x-ray therapy from miniature x-ray tubes, the apparatus may also be used with isotopes to similar effect. From the embodiments described herein, other features, apparatus configurations and procedures will be apparent to those of skill in the art. Such improvements are to be considered within the scope of this invention.

DESCRIPTION OF THE PREFERRED EMBODIMENTS

Figure 1:
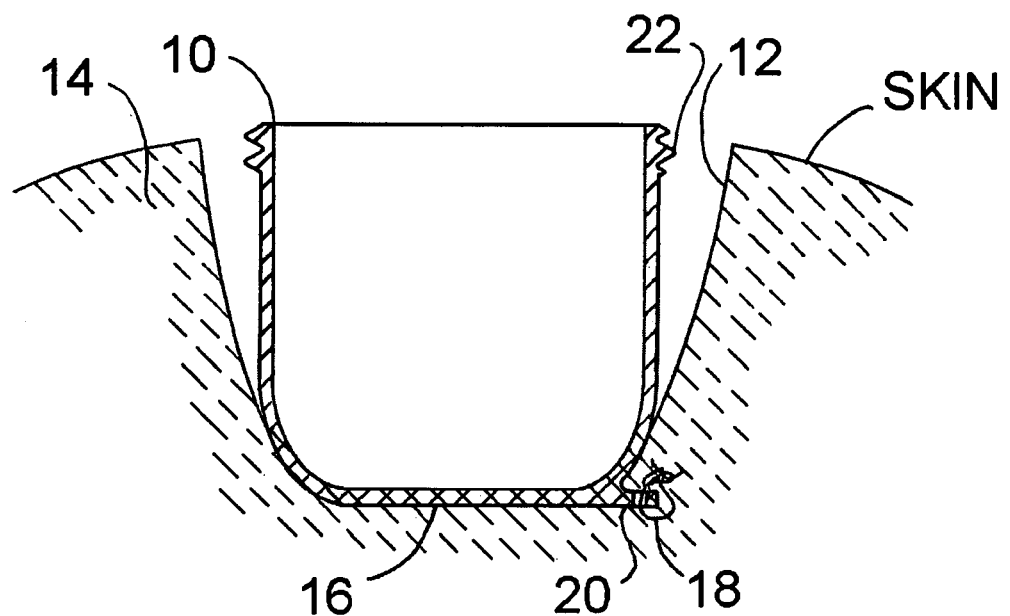
FIG. 1 depicts in cross section a simple cup embodiment of the invention positioned within the breast of a patient and sutured therein using suture tabs provided for this purpose.

FIG. 1 shows in section view, a preferred brachytherapy applicator cup 10 positioned in an open surgical cavity 12 left in the breast 14 of a patient following (at least partial) tumor resection. The cup preferably is substantially rigid, of a predetermined shape (in this example circular), and preferably substantially transparent to x-rays and to visible light, or at least partially transparent to x-rays. It may, for example, be molded from engineering plastic, preferably with a specific gravity near unity to simplify treatment planning Suitable materials would include polycarbonate, polyphenolene ether (Noryl, from GE Plastics, is an example) and polyethersulfone (Radel, from Solvay Advanced Polymers is another example). The shape can be generally circular-cylindrical, or other shapes.

If the tissues at the bottom of the cavity are susceptible to radiation damage and are to be protected, the material of the bottom portion 16 of the cup may further comprise the addition of attenuating fillers (see cross-hatching at bottom portion 16) to shield such tissues, or alternatively, an attenuating coating can be applied to the bottom of the cup. Barium compounds or metallic particulates may be used for filling purposes, but the separate filled and unfilled portions of the cup may require separate molding and subsequent joining together, as by bonding for example.

The distal bottom of the cup is positioned at the bottom of the cavity and if desired, secured with conventional sutures 18 to maintain cup orientation within the surgically created cavity. An optional flange or tabs 20 may be provided for suturing purposes. Alternatively, a base (not shown) to be located under the cup may be sutured similarly in the bottom of the cavity. The cup bottom can be retained to the base by a suitable releasable attachment means. For example, the base may comprise half of a conventional hook and loop fastener (VELCRO), to which a mating fastener portion secured to the outside of the bottom of the cup, such as by bonding, is used to anchor the cup in the cavity. In another variation where a base is used, the bottom of the cup could comprise half of either a screw-thread or snap-on fastener and be attached to the base by mating screw thread or snap-on fixation. It is also possible the cup could be inverted and its open mouth screwed onto such a threaded base, with apparatus described below emerging from the upper side, which would be the cup bottom. It is also possible to use a vessel which is permanently closed but with a top opening to accommodate the radiation apparatus described below; for small resection cavities the vessel could comprise a solid mass of plastic material with a guide channel extending into it from the outer side. The term vessel is intended to include such a configuration of an applicator.

In instances where the tissues under the cup are to be shielded from radiation, rather than filling the cup bottom with attenuating material, one or both portions of the hook and loop fastener or the base sutured to the bottom of the cavity may further comprise a shielding layer, for example a layer of metallic foil or filled polymer.

A range of applicator cup sizes and shapes may be offered as standard, from which the surgeon or radiation oncologist may choose to fit the patient's resection cavity, or in the alternative, and where there is sufficient time and information available, a cup can be fabricated which addresses a particular patient's requirement. Proximate to the cup's lip are screw threads 22 to mate with the lid (not shown in this drawing) presuming the cup is circular as shown. If the cup is not of circular cross-section, conventional over-center or snap-on fasteners can be used with features molded into the cup and lid for the purpose, which can be as in plastic food storage containers.

Figure 2:
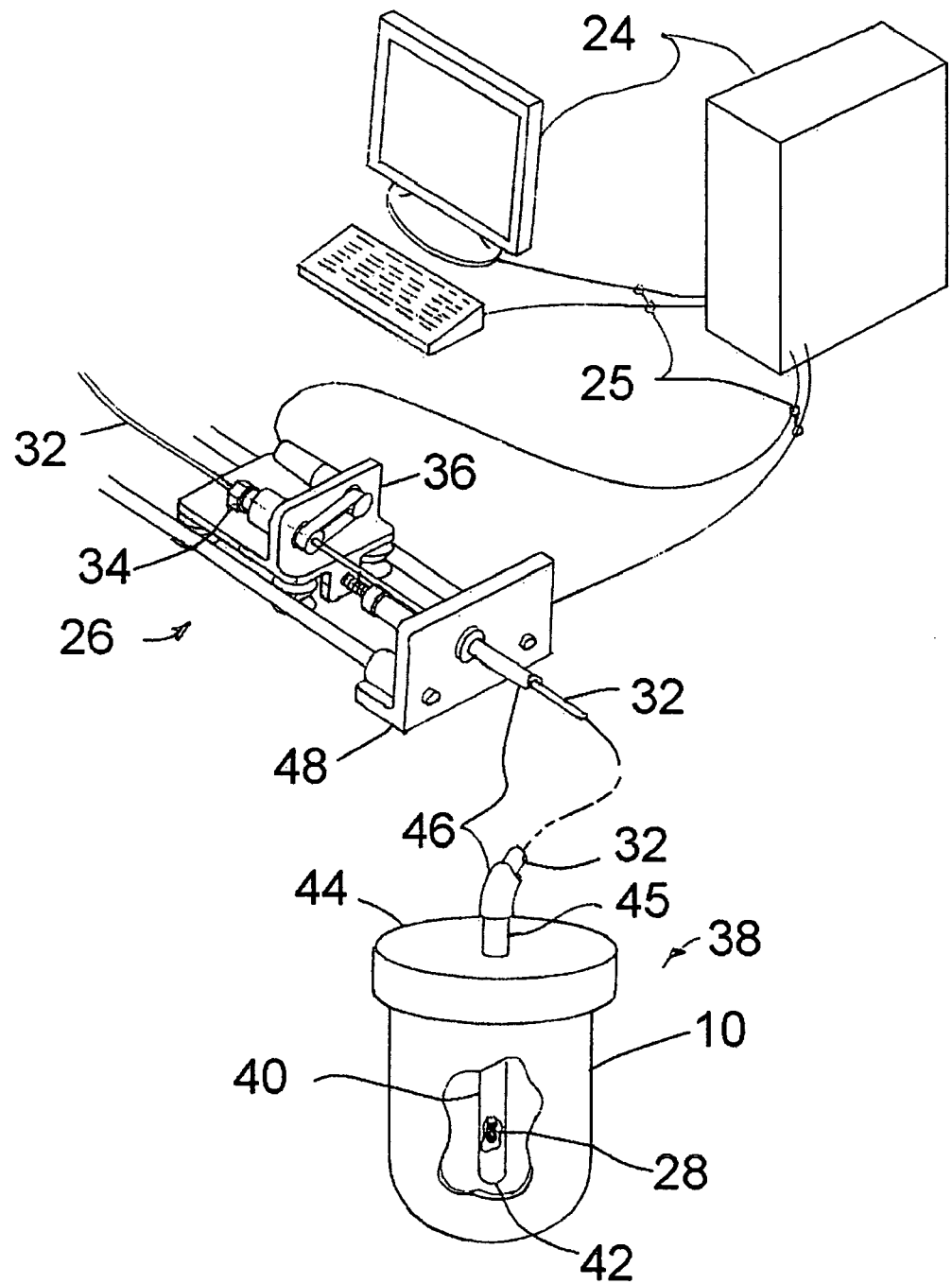
FIG. 2 shows schematically in perspective a brachytherapy treatment system including an applicator apparatus of the invention.

FIG. 2 shows the principal elements of the treatment system schematically. The elements comprise a treatment planning computer 24 used to create an optimized treatment plan based on the dose prescription and on cup shape, and if conventional imaging is performed prior to planning, also on other relevant information from the imaging data. Imaging information, particularly if by CT methods, may also reveal tissue conformance to the cup 10 and location of anatomy which may require shielding or other accommodation. The computer 24 may, in one form of the system, then provide the treatment plan to the controller (not shown) which manages control of the source output, source position spatially and the timing of exposure from radiation emissions in order to deliver the prescribed treatment. Parts of the computer 24, controller and other elements of the treatment system communicate by conventional wiring 25, and ultimately source positioning is controlled through a mechanical manipulator 26 which positions the source 28 as needed within the cup and therefore within the resection cavity. The computer and controller can be a single component, and the term "controller" as used in the claims and sometimes herein is intended to refer to either implementation.

With the preferred miniature x-ray tube sources, the source 28 is usually contained and carried within a source catheter 32 to which the source is rigidly affixed. The catheter 32 is shown positioned in the collet 34 on the sled 36 of the controlled portion of the manipulator. Where required, conventional fluid cooling apparatus (not shown) is provided, and cooling fluid is supplied at the manipulator apparatus from whence it flows to the x-ray source itself within the catheter.

The applicator 38 of the system comprises a tubular source guide 40 which is preferably rigid and transparent to radiation. The distal end 42 of the source guide is closed. Proximally, the source guide 40 is affixed to the lid 44 of the cup 10. The source guide distal end 42 is thus positioned in the cup 10 when the lid is in place. The proximal end 45 of the source guide connects to a flexible extension 46 of the source guide that preferably is anchored to a stationary portion 48 of the manipulator 26. This establishes a constant source guide lumen length from the manipulator to the source guide distal end 42 positioned within the applicator cup such that the controller can precisely control manipulation of the source 28 within the source guide 40, in the manner of a control cable. The cup 10 and the lid 44 of the applicator 38 are shown assembled as if positioned in the patient's breast or the anatomy (not shown). The source guide portion within the cup is preferably straight, but need not be if necessary to accommodate a non-uniform prescription.

In explanation, control cables of the sort described above with respect to source manipulation are sometimes called Bowden cables, and comprise a flexible tubular outer sheath of fixed length, the ends of which are fixed to two different structures whose relative position need not be either constant or predetermined. Within the control cable sheath is a wire (or in this case, source catheter 32) which can be translated axially. Pushing or pulling a given amount on one end of the wire results in a substantially identical displacement at the other end of the wire. An automobile throttle cable is a common example of such a control cable.

Figure 3:
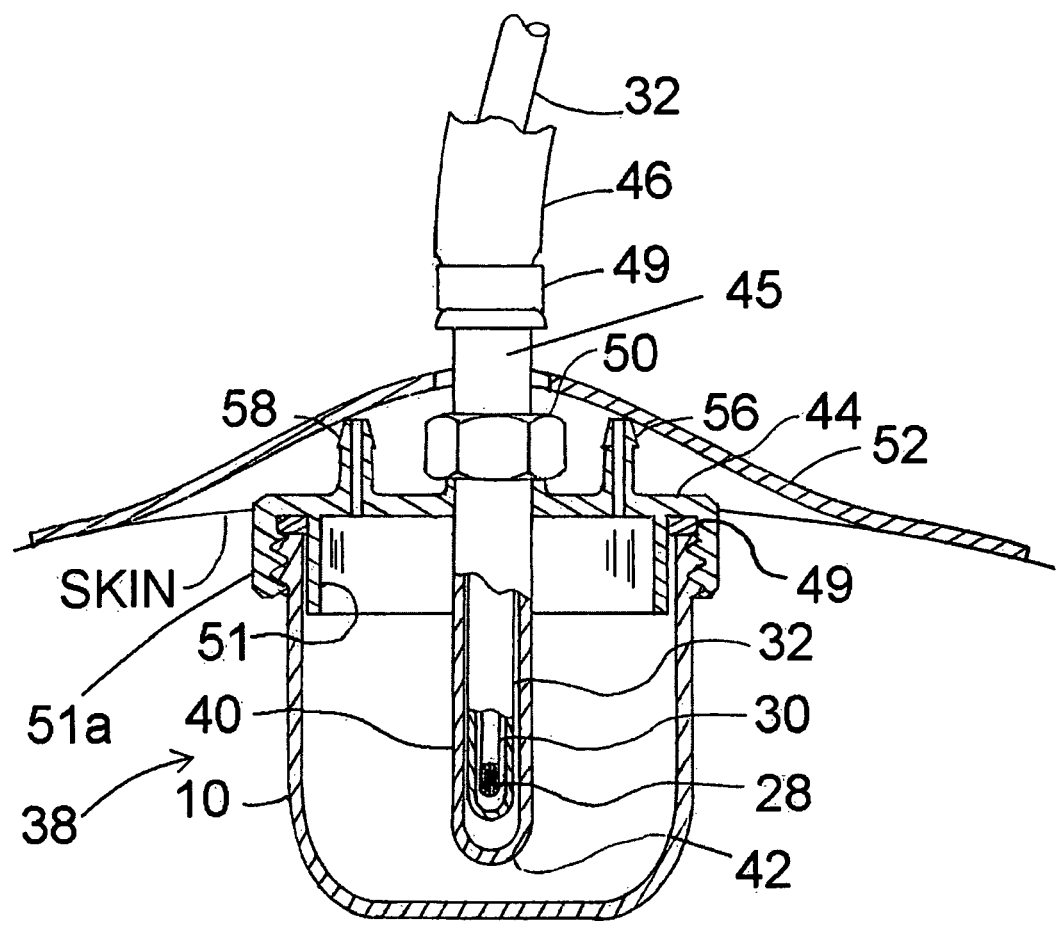
FIG. 3 shows in cross section breast tissues gathered around the applicator with the cup, a lid and gasket assembled and a flexible extension of the source guide leading to an outside manipulator.

In FIG. 3 the applicator 38 is shown submerged in a cavity of tissue such as a breast 14. The tissues of the breast 14 have been gathered around the cup 10 and lid 44 and are held in place by conventional tape, sutures, or other conventional methods familiar to surgical practice. The lid 44 of the cup 10 is shown assembled to the cup with a gasket 49, for example of silicone, positioned between cup and lid to seal the volume within. The lid has the central source guide 40 preferably affixed to the lid by conventional methods, an example of which is a collet 50, and extending into the cup, with the proximal end 45 secured to the flexible extension 46 by a conventional clamp 49. If necessary to protect the patient's skin and near-skin tissues from overdose which could result in adverse cosmeses, the lid can further comprise a skirt 51 of a shielding material extending coaxially inside the lip of the cup to a depth sufficient to protect the skin and near-skin tissues as shown. Alternatively, the cap's threaded skirt 51*a* could include shielding material. A flexible drape 52 according to the teachings of U.S. patent application Ser. No. 11/323,331 is shown draping the breast 14 to protect attending personnel. The lid 44 may also be of a shielding material in order to provide radiation exposure protection to therapeutic personnel, either as a single molding as shown, or alternatively, the lid can comprise an assembly of parts. Depending on the attenuating properties of the lid elements, which include the threaded skirt 51*a*, the attenuating skirt 51 may be redundant and can be eliminated. Also shown on the top of the lid is a vent 56 to permit air to escape from the interior volume of the applicator as the cup is filled with attenuating medium through an inlet port 58.

Figure 4:
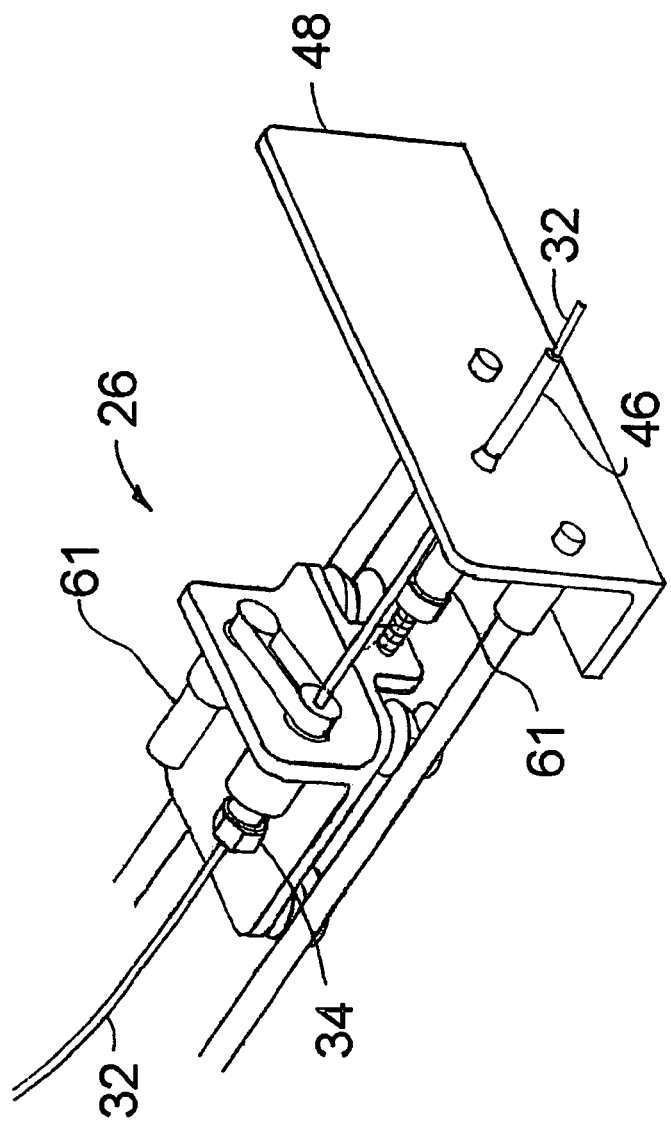
FIG. 4 is a perspective view showing a source catheter positioned in the manipulator and flexible source guide extension in preparation for controlled delivery of radiotherapy.

FIG. 4 shows in greater detail the manipulator apparatus 26. The proximal end of the source guide flexible extension 46 is mounted to the stationary portion 48 of the manipulator. The source catheter 32 is shown positioned within the collet 34 and extending into the source guide extension 46. The source catheter 32 and hence the source (not shown) are controlled spatially by servomotors 61 of the manipulator in response to commands from the controller or computer. The manipulator shown schematically in FIG. 4 can accommodate both translation of the source axially within the source guide as well as rotation relative to the source guide, the latter for use with x-ray tubes emitting only through a solid angle (directional) rather than isotropically. In instances where isotropic source are used, only axial manipulation is required and the rotational capability of the manipulator 26 as shown may be eliminated. Furthermore, if it is desired to translate the source within the source catheter, a second manipulator (not shown) similar to the manipulator 26 may be added to operate in tandem with the manipulator 26 and provide independent control for both source and catheter.

Figure 5:
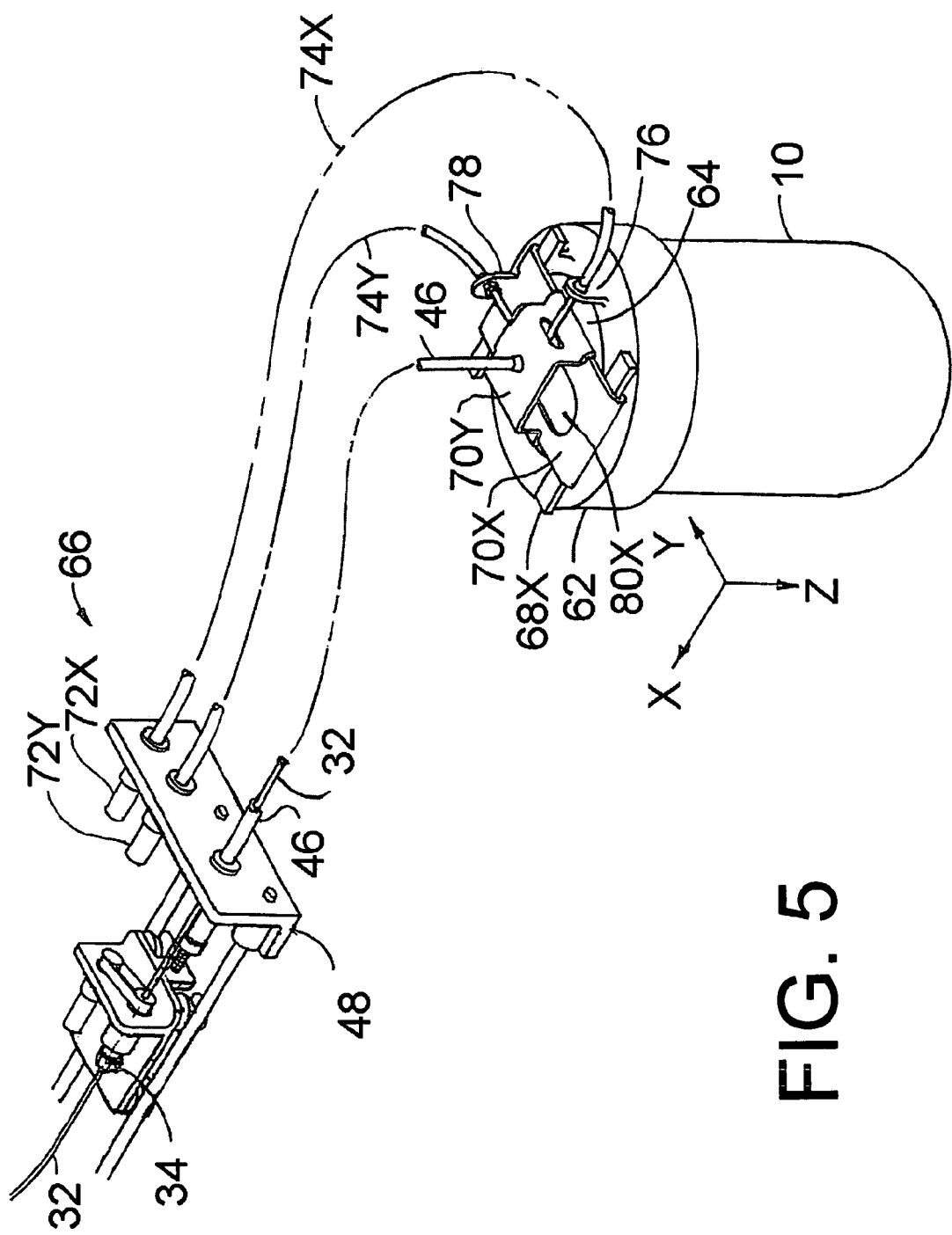
FIG. 5 is a perspective view showing schematically an applicator lid with provision for X/Y manipulation of the source guide, and control wires for connection to actuators for X/Y manipulation.

FIG. 5 depicts schematically a lid embodiment and system where the top of the lid 62 comprises a membrane 64, for example of silicone, to seal the volume within the cup 10 while the source guide (not shown) is translated in the X and/or Y directions by a servomotor positioning apparatus 66 mounted on the stationary portion 48 of the manipulator apparatus. Applicator guide rails 68X, integral parts of the lid 62, guide a X sled 70X in the X direction, while the edges of the sled 70X guide a sled 70Y in the Y direction. Both sleds are controlled by servomotors 72X and 72Y respectively, acting through control cables 74X and 74Y of the sort described above. The servomotors 72X and 72Y are responsive to commands from the central controller. Collectively, this apparatus serves to keep the source guide parallel to the axis of the cup during X/Y translation. In principle such X/Y apparatus could be mounted entirely on the lid of the applicator, but given any substantial bulk or weight for the positioning apparatus, it is preferable to mount the positioning servomotors remotely, for example on the stationary portion 48 of the manipulator apparatus as shown.

In this embodiment, the proximal end of each of the control cable 74X and 74Y sheaths is affixed to the stationary portion 48 of the manipulator apparatus, as is the proximal end of the source guide flexible extension 46. The source catheter 32 is mounted in the collet 34 and leads into the flexible source guide extension 46. The distal end of the sheath of the cable 74X is fastened to a mounting tab 76 on the lid 62. The distal end of the sheath of cable 74Y is mounted on a tab 78, an integral part of the sled 70X. The proximal ends of the inner wires of the two cables are controlled by the axial servomotors 72X and 72Y. The distal end of the inner wire of the cable 74X is connected to a tab (not shown) proximate the central slot 80X of the sled 70X. The distal end of the inner wire of the cable 74Y connects to a tab 82 on the sled 70Y (see FIG. 6 for detail). With this arrangement, and together with manipulation of the source catheter 32, the source may be positioned anywhere within the cup 10 by X,Y,Z coordinates which fall within the mechanical limits of the apparatus.

Although the source guide manipulation above is limited to X and Y translation, other manipulation strategies can be used, for example by pivoting an arm mounting the source guide 40, where the radius of the source guide from the pivot and the pivot angle are controlled. It is also possible to vary the angle of the source guide axis relative to the cup axis. Servomotors can be used to control the positions of all these variations in keeping with the degrees of freedom of motion provided by the apparatus. Still other control schemes will be readily apparent to those of skill in the art. If desired, closed loop feedback control for each degree of freedom employed can be provided easily, for example by use of linear variable differential transformer (LVDT) sensors, the output of which can be used to verify position with precision. Sensor outputs can also be used to verify treatment to plan. Such methods are known to those of skill in the art.

Figure 6:
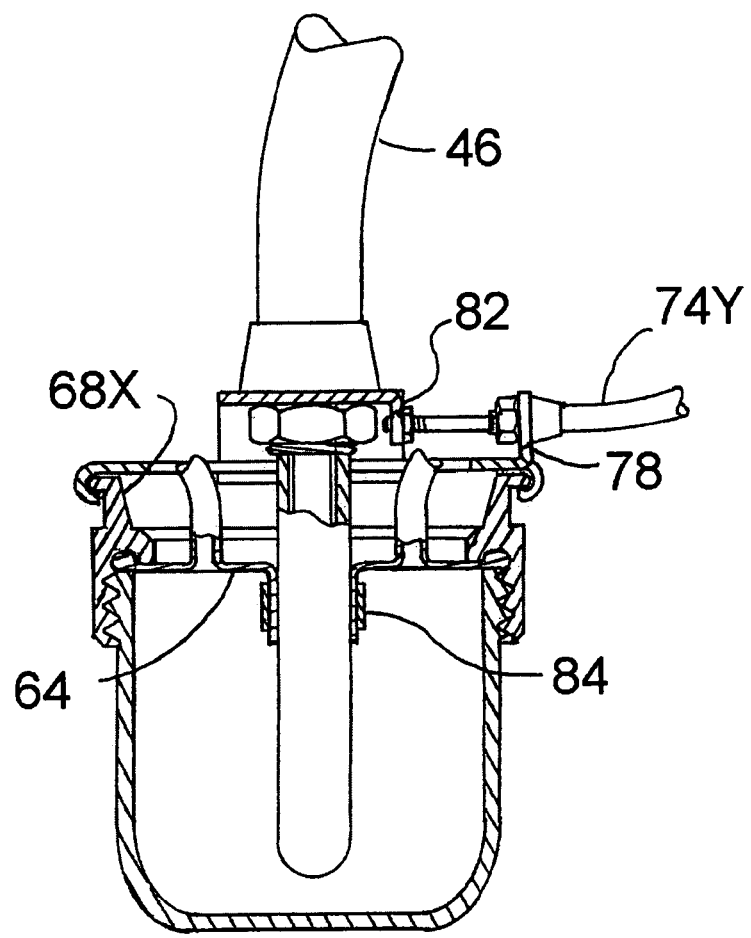
FIG. 6 shows schematically in cross section, detail of the applicator of FIG. 5.

FIG. 6 is a cross section detail through the axis of the source guide 40, looking in the X direction. The membrane 64 is shown clamped onto the source guide 40 by a clamp 84. The mounting of the sled 70X on the rails 68X is seen in FIG. 6.

Various embodiments employing combinations of features described above are useful for IORT. The simplest case is a source guide positioned in a fixed position within a cup of circular cross-section, and a substantially isotropic source in a fixed position or translated within the source guide. Special circumstances can be accommodated with other embodiments. For example, if the resection cavity from tumor removal results in a cavity which is not centered on the tumor location, as discussed above, perhaps as a result of successive adverse pathology findings or for any other reason, the prescription can be centered on the tumor location by use of a source guide passing through the tumor location rather than being centered within the cavity. The cup and lid can still be chosen to fill the cavity, be it round or oval in cross section, or of another shape. Since the likelihood of disease infiltration into apparently normal tissue decreases with distance from the tumor, when using this approach, the farthest tissues from the tumor will receive a lighter dose. To the extent that a portion of the target tissue limits fall within the cup, the tissues beyond may receive very little dose, while the tissues nearer the tumor will receive the full prescription. With the embodiment described in FIG. 5, the isodose pattern circumscribing the prescription may be sculpted beyond shapes available from a fixed source position or from a linear source guide within which the source is translated.

Although described particularly in relation to breast radiation, the applicator and accompanying control apparatus can be used at other tissue locations wherein a resection cavity or other cavity is open at the skin.

The embodiments described above will suggest to those of skill in the art, other combinations of features which, when combined, will result in further embodiments. These embodiments are to be considered within the scope of the invention.

The invention claimed is:

1. A device for administering brachytherapy to the tissue of a living patient, comprising:
a cup of a material at least partially transparent to x-ray radiation and having a longitudinal cup axis;
a lid for threaded engagement with the cup and including a peripheral threaded downwardly depending section having a free end;
a source guide for receiving an x-ray source attached to and penetrating through the lid of the cup and extending along a source guide longitudinal axis that is coincident with the longitudinal cup axis;
a catheter carrying an x-ray source slidable within the source guide in the cup;
wherein the cup can be positioned in an open resection cavity so that the catheter can be manipulated axially within the source guide in the cup;
a manipulator for moving the source guide so that the x-ray source can be moved to different positions within the cup during the brachytherapy treatment; and
a skirt formed integrally with the lid and extending coaxially with the cup axis;
said skirt formed as a downwardly depending annular wall member having a free lower end that terminates at substantially the same location as the peripheral threaded downwardly depending section free end of the lid;
wherein the skirt is constructed of an attenuating material to protect the skin of the patient against radiation.

2. The device of claim 1 wherein the peripheral threaded downwardly depending section of the skirt is disposed within the cup.

3. The device of claim 1 wherein the lid has threads that are internal and the cup has threads that are external.

4. A device for administering brachytherapy to the tissue of a living patient, comprising:
a vessel formed of a material at least partially transparent to x-ray radiation, with a substantially closed outer end on the vessel and an internal chamber;
a source guide having proximal and distal ends with the proximal end disposed outside of the vessel and the distal end extending into the vessel, the source guide for receiving an x-ray source and extending along a source guide longitudinal axis;
a catheter carrying an x-ray source and positioned within the source guide in the vessel, wherein the vessel can be positioned in an open resection cavity, and with the x-ray source positioned within the source guide in the vessel so that brachytherapy treatment can be administered to tissues surrounding the vessel; and
a manipulator for moving the source guide so that the x-ray source is moved to different lateral positions within the internal chamber of the vessel during the brachytherapy treatment so as to cover a total chamber coverage area that is greater than the area of the source guide itself;
said manipulator constructed and arranged for lateral movement that is substantially transverse to the source guide longitudinal axis.

5. The device of claim 4 wherein the vessel is comprised of a cup and cover having a common longitudinal vessel axis that is coincident with the source guide axis.

6. The device of claim 5 wherein the manipulator includes provision for moving the source guide in at least one of X and Y directions of translation within the cup, the X and Y directions being parallel to the cover, so that the x-ray source can be moved to different positions within the cup during the brachytherapy treatment.

7. The device of claim 5 wherein the manipulator includes provision for moving the source guide in X and Y directions of translation within the cup, the X and Y directions being parallel to the cover, so that the x-ray source can be moved to essentially any position within the cup during the brachytherapy treatment.

8. The device of claim 4 wherein the manipulator controls the source guide to different lateral positions that are parallel to the vessel closed outer end.

9. The device of claim 4 wherein the manipulator is constructed and arranged for pivotally supporting the source guide for control of a pivot angle of the source guide.

10. A device for administering brachytherapy to the tissue of a living patient, comprising:
a vessel formed of a material at least partially transparent to x-ray radiation, with a substantially closed outer end on the vessel and an internal chamber;
a source guide having proximal and distal ends with the proximal end disposed outside of the vessel and the distal end extending into the vessel, the source guide for receiving an x-ray source and extending along a source guide longitudinal axis;
a catheter carrying an x-ray source and positioned within the source guide in the vessel, wherein the vessel can be positioned in an open resection cavity, and with the x-ray source positioned within the source guide in the vessel so that brachytherapy treatment can be administered to tissues surrounding the vessel; and
a manipulator for moving the source guide so that the x-ray source is moved to different lateral positions within the internal chamber of the vessel during the brachytherapy treatment so as to cover a total area that is greater than the area treated when the source guide is stationary;
said manipulator constructed and arranged for lateral movement that is substantially transverse to the source guide longitudinal axis.

11. The device of claim 10 wherein the vessel is comprised of a cup and cover having a common longitudinal vessel axis that is coincident with the source guide axis.

12. The device of claim 11 wherein the manipulator includes provision for moving the source guide in at least one of X and Y directions of translation within the cup, the X and Y directions being parallel to the cover, so that the x-ray source can be moved to different positions within the cup during the brachytherapy treatment.

13. The device of claim 11 wherein the manipulator includes provision for moving the source guide in X and Y directions of translation within the cup, the X and Y directions being parallel to the cover, so that the x-ray source can be moved to essentially any position within the cup during the brachytherapy treatment.

14. The device of claim 10 wherein the manipulator controls the source guide to different lateral positions that are parallel to the vessel closed outer end.

15. The device of claim 10 wherein the manipulator includes a pivot arm for supporting the source guide for control of a pivot angle of the source guide.

\* \* \* \* \*